United States Patent [19]

Yoshikawa et al.

[11] Patent Number: 5,756,869
[45] Date of Patent: May 26, 1998

[54] METHOD OF PREPARING HYDROFLUOROCARBON

[75] Inventors: Satoshi Yoshikawa; Naoto Takada; Hideki Oshio, all of Kawagoe, Japan

[73] Assignee: Central Glass Company Limited, Yamaguchi, Japan

[21] Appl. No.: 742,965

[22] Filed: Nov. 1, 1996

Related U.S. Application Data

[63] Continuation of Ser. No. 434,363, May 5, 1995, abandoned.

[51] Int. Cl.$^6$ ............................................ C07C 19/08
[52] U.S. Cl. ................................................ 570/176
[58] Field of Search ..................................... 570/176

[56] References Cited

U.S. PATENT DOCUMENTS 5,326,914  7/1994  Baker ........................ 570/176

FOREIGN PATENT DOCUMENTS 0580181  1/1994  European Pat. Off. ............ 570/176
2-204443  8/1990  Japan.
2-207038  8/1990  Japan.
4-99738   3/1992  Japan.

*Primary Examiner*—Alan Siegel
*Attorney, Agent, or Firm*—Evenson, McKeown, Edwards & Lenahan, P.L.L.C.

[57] ABSTRACT

The invention relates to a method of preparing a saturated hydrofluorocarbon represented by $C_nH_pF_z$, by reducing a chlorofluorocarbon or hydrochlorofluorocarbon represented by $C_nH_xCl_yF_z$ by hydrogen in the presence of a catalyst having palladium and bismuth, wherein "n" is an integer within a range from 3 to 6, "x" is an integer within a range from 0 to 2n, each of "y" and "z" is an integer within a range from 1 to 2n+1, x+y+z=2n+2 or 2n, p=x+y when x+y+z=2n+2, and p=x+y+2 when x+y+z=2n. The catalyst has a long lifetime in the reduction. According to the invention, conversion of the chlorofluorocarbon or hydrochlorofluorocarbon is high, and the saturated hydrofluorocarbon is prepared with a high yield and a high selectivity.

15 Claims, No Drawings

METHOD OF PREPARING HYDROFLUOROCARBON

This is a continuation application of Ser. No. 08/434,363, filed on May 5, 1995, now abandoned.

BACKGROUND OF THE INVENTION

The present invention relates to a method of preparing a hydrofluorocarbon (HFC) which is useful as a foaming agent for preparing polyolefin foam, polystyrene foam, polyurethane foam, polyisocyanurate foam or the like, a refrigerant of air conditioner, refrigerator or chiller unit, a detergent solvent for flux, fats or oils, another solvent such as reaction solvents or the like, and more particularly to a method of preparing a saturated HFC from chlorofluorocarbon (CFC) or hydrochlorofluorocarbon (HCFC) in the presence of catalyst. This method belongs to a catalytic reduction.

Recently, there has been an increasing demand for a method of preparing saturated HFC(s) as alternatives for CFC(s) used as refrigerant, foaming agent, aerosol propellant, solvent and the like, in an industrial scale and an economical way. For example, JP-A-2-207038 discloses a method of preparing 1,1,2,2,3-pentafluoropropane (hereinafter, this compound will be referred to as HFC245ca). In this method, 1,1,3-trichloro-2,2-difluoropropane is fluorinated by potassium fluoride so as to prepare HFC245ca. However, HFC245ca prepared by this method is relatively low in selectivity and yield thereof. Therefore, this method may not be suitable for an industrial scale production thereof.

JP-A-2-204443 discloses another method of preparing HFC245ca. In this method, 1-chloro-1,2,2,3,3-pentafluoropropane is reduced by hydrogen in the presence of a catalyst of palladium carried on activated carbon so as to prepare HFC245ca. As is disclosed in this method, the use of palladium as a catalyst for hydrodechlorination is generally known. However, this catalyst is generally short in lifetime in the reaction. Therefore, it has been difficult to use this catalyst in an industrial scale production of HFC245ca.

JP-A-4-99738 proposes a method of preparing trifluoroethylene, in which 1,1,2-trichloro-1,2,2,-trifluoroethane is reduced by hydrogen in the presence of palladium and at least one element selected from the group consisting of gold, tellurium, antimony, bismuth and arsenic. This reaction is a catalytic hydrogenation with the elimination of hydrogen chloride. In this method, trifluoroethylene which is an unsaturated HFC is selectively produced. Thus, it is necessary to hydrogenate this trifluoroethylene so as to prepare the above-mentioned saturated fluorohydrocarbon. Therefore, the above two steps of hydrogenation are necessary to prepare this saturated HFC. This increases the production cost thereof.

SUMMARY OF THE INVENTION

It is an object of the present invention to provide an improved method of preparing a saturated HFC having 3–6 carbon atoms from a HFC or HCFC, by only one reaction in the presence of a catalyst.

According to the present invention, there is provided a method of preparing a saturated HFC represented by the following general formula (1), the method comprising the step of:

reducing a CFC or HCFC represented by the following general formula (2), by hydrogen in the presence of a catalyst having palladium and bismuth.

$$C_nH_pF_z \qquad (1)$$

$$C_nH_xCl_yF_z \qquad (2)$$

wherein "n" is an integer within a range from 3 to 6, "x" is an integer within a range from 0 to 2n, each of "y" and "z" is an integer within a range from 1 to 2n+1, x+y+z=2n+2 or 2n, p=x+y when x+y+z=2n+2, and p=x+y+2 when x+y+z=2n.

The inventors have unexpectedly found that, in the presence of the above special catalyst, hydrogenation of the above CFC or HCFC with the replacement of chlorine by hydrogen, not with the elimination of hydrogen chloride, occurs selectively so that the above saturated HFC is selectively formed with a high field by only one reaction (hydrogenation), and that the above catalyst's lifetime is sufficiently long in the hydrogenation.

In particular, as are exemplified in the following Examples, the inventors have unexpectedly found that, in the presence of the above special catalyst, hydrogenations of 1,3-dichloro-1,1,2,2,3-pentafluoropropane, 3,3-dichloro-1,1,1,2,2-pentafluoropropane, 1,3-dichloro-1,1,2,2,3,3-hexafluoropropane, 1,1,3-trichloro-1,2,2,3,3-pentafluoropropane and 2,3-dichloro-1,1,1,4,4,4-hexafluorobutene-2, with the replacement of chlorine by hydrogen, occur respectively selectively so that 1,1,2,2,3-pentafluoropropane, 1,1,1,2,2-pentafluoropropane, 1,1,2,2,3,3-hexafluoropropane, 1,1,2,2,3-pentafluoropropane, and 1,1,1,4,4,4-hexafluorobutane are respectively formed with substantially high yield and selectivity.

DESCRIPTION OF THE PREFERRED EMBODIMENTS

A method of preparing a saturated HFC represented by the following general formula (1) will be described in the following in accordance with the present invention. This method comprises the step of: reducing a CFC or HCFC represented by the following general formula (2), by hydrogen in the presence of a catalyst having palladium and bismuth,

$$C_nH_pF_z \qquad (1)$$

$$C_nH_xCl_yF_z \qquad (2)$$

wherein "n" is an integer within a range from 3 to 6, "x" is an integer within a range from 0 to 2n, each of "y" and "z" is an integer within a range from 1 to 2n+1, x+y+z=2n+2 or 2n, p=x+y when x+y+z=2n+2, and p=x+y+2 when x+y+z=2n.

HCFC or CFC which is a raw material of the method of the present invention contains chlorine and fluorine atoms, may have a straight-chain or branched-chain structure, and is a saturated or unsaturated aliphatic hydrocarbon or a saturated or unsaturated cyclic hydrocarbon. When HCFC or CFC is reduced, it is possible that only chlorine atom(s) of HCFC or CFC is reduced, without the reduction of fluorine atom(s) of HCFC or CFC. It is easily expected that HFC can be prepared from a hydrocarbon containing another halogen atom such as bromine or iodine, by the method of the present invention.

CFC or HCFC having three carbon atoms will be represented by the following general formula (3):

$$C_3H_xCl_yF_z \qquad (3)$$

wherein "x" is an integer within a range from 0 to 6, each of "y" and "z" is an integer within a range from 1 to 7, x+y+z=8 or 6. This CFC or HCFC is chlorofluoropropane or chlorofluoropropene. Examples of this CFC are 1,1,3-trichloro-1,2,2,3,3-pentafluoropropane, 1,3-dichloro-1,1,2,2,3,3-hexafluoropropane, 1,1,1-trichloro-2,2,3,3,3-pentafluoropropane, 1,1-dichloro-1,2,2,3,3,3-hexafluoropropane, 1-chloro-1,1,2,2,3,3,3-heptafluoropropane, 1,1,1,2-tetrachloro-2,3,3,3-tetrafluoropropane, 1,1,2-trichloro-1,2,3,3,3-pentafluoropropane, 1,2-dichloro-1,1,2,3,3,3-hexafluoropropane, 1,1,13-tetrachloro-2,2,3,3-tetrafluoropropane, 1,1,2,3-tetrachloro-1,2,3,3-tetrafluoropropane, 1,2,3-trichloro-1,1,2,3,3-pentafluoropropane, 1,1,3,3-tetrachloro-1,2,3,3-tetrafluoropropane, 1,1,3-trichloro-1,2,3,3,3-pentafluoropropane, 1,1,1,3,3-pentachloro-2,2,3-trifluoropropane, 1,1,3,3-tetrachloro-1,2,2,3-tetrafluoropropane, 1,3-trichloro-1,1,2,2,3-pentafluoropropane, 1,1,1,2,3-pentachloro-2,3,3-trifluoropropane, 1,1,2,3-tetrachloro-1,2,3,3-tetrafluoropropane, 1,2,3-trichloro-1,1,2,3,3-pentafluoropropane, 3-chloropentafluoropropene-1, 2-chloropentafluoropropene-1, 1-chloropentafluoropropene-1, 1,1-dichlorotetrafluoropropene-1, 1,2-dichlorotetrafluoropropene-1, 1,3-dichlorotetrafluoropropene-1, 3,3,3-trichlorotrifluoropropene-1, 1,1,3-trichlorotrifluoropropene-1, 1,1,2-trichlorotrifluoropropene, and isomers of these compounds.

Hydrogen atom(s) may be partly substituted for chlorine atom(s) of the above exemplary compounds of $C_3H_xCl_yF_z$.  These hydrogen-substituted compounds and a mixture(s) of the hydrogen-substituted compound(s) and the above exemplary compound(s) may be used as a raw material equivalent to CFC. Examples of the hydrogen-substituted compounds are 3,3-dichloro-1,1,1,2,2-pentafluoropropane, 1,3-dichloro-1,1,2,2,3-pentafluoropropane, 1,1-dichloro-1,2,2,3,3-pentafluoropropane, 1-chloro-1,2,2,3,3-pentafluoropropane, 1-chloro-2,2,3,3,3-pentafluoropropane, 1-chloro-1,1,2,2,3-pentafluoropropane, 1-chloro-2,3,3,3-tetrafluoropropene-1, 1,1-dichloro-3,3,3-trifluoropropene-1, 1,3-dichloro-2,3,3-trifluoropropene-1, and 1,2-dichloro-3,3,3-trifluoropropene-1.

CFC or HCFC having four carbon atoms will be represented by the following general formula (4):

$$C_4H_xCl_yF_z \qquad (4)$$

wherein "x" is an integer within a range from 0 to 8, each of "y" and "z" is an integer within a range from 1 to 9, x+y+z=10 or 8. This CFC or HCFC is chlorofluorobutane or chlorofluorobutene. Examples of this CFC are chlorononafluorobutane, 1,1-dichlorooctafluorobutane, 2,2-dichlorooctafluorobutane, 2,3-dichlorooctafluorobutane, 2,2,3-trichloroheptafluorobutane, 1,2,4-trichloroheptafluorobutane, 2,2,3,3-tetrachlorohexafluorobutane, 1,2,3,4-tetrachlorohexafluorobutane, 1,2,2,3-tetrachlorohexafluorobutane, 1,1,3,4-tetrachlorohexafluorobutane, 1,1,1,3,3-pentachloropentafluorobutane, 1,1,3,3,4-pentachloropentafluorobutane, 1,1,1,3,3,3-hexachlorotetrafluorobutane, 1,2,2,3,3,4-hexachlorotetrafluorobutane, 1,1,2,3,4,4-hexachlorotetrafluorobutane, 1,1,1,3,3,4-hexachlorotetrafluorobutane, 1,1,1,2,2,3,3-heptachlorotrifluorobutane, 1,1,2,2,3,3,4-heptachlorotrifluorobutane, 1,1,1,2,2,4,4,4-octachlorodifluorobutane, 1,1,1,2,2,3,3,4-octachlorodifluorobutane, 2-chloroheptafluorobutene-2, 2,3-dichloro-1,1,1,4,4,4-hexafluorobutene-2, 1,4-dichloro-1,1,2,3,4,4-hexafluorobutene-2, 4,4-dichloro-1,1,2,3,3,4-hexafluorobutene-2, 3,4-dichloro-1,1,2,3,4,4-hexalfuorobutene-2, 2,4,4-trichloro-pentafluorobutene-2, 2,2,3-trichloropentafluorobutane, 1,3,4,4-tetrachlorotetrafluorobutene-1, 2,2,4,4-tetrachlorotetrafluoro-butene-1, and isomers of these compounds.

Hydrogen atom(s) may be partly substituted for chlorine atom(s) of the above exemplary compounds of $C_4H_xCl_yF_z$.  These hydrogen-substituted compounds and a mixture(s) of the hydrogen-substituted compound(s) and the above exemplary compound(s) may be used as a raw material equivalent to CFC. Examples of the hydrogen-substituted compounds of $C_4H_xCl_yF_z$ are 1-chloro-1,1,2,2,3,3,4,4-octafluorobutane, 1,1-dichloro-2,2,3,3,4,4,4-heptafluorobutane, 2,2,3-trichloro-1,1,1,3,3,3-hexafluorobutane, 3,3,3-trichloro-1,1,1-trifluoro-1-trifluoromethylpropane, 1,1,2,2,3,3,4-heptachloro-4,4-difluorobutane, 1-chloro-2,2,3,3,4,4,4-heptafluorobutane, 1,2-dichloro-2,3,3,4,4,4-hexafluorobutane, 2,3-dichloro-1,1,1,4,4,4-hexafluorobutane, 1,1,1-trichloro-2,2,4,4,4-pentafluorobutane, 1,1,1,2,2-pentachloro-4,4,4-trifluorobutane, 2-chloro-1,1,1,4,4,4-hexafluorobutane, 1,3-dichloro-1,1,4,4,4-pentafluorobutane, 1,1,1-trichloro-2,2,3,3-tetrafluorobutane, 2-chloro-1,1,1,4,4,4-hexafluorobutene-2, 4-chloro-1,1,2,3,3,4-hexafluorobutene-1, 1,3,4-trichloro-1,3,4,4-tetrafluorobutene-1, and 1,1,1,2-tetrachloro-1,1,1-trifluorobutene-2.

CFC or HCFC having five carbon atoms will be represented by the following general formula (5):

$$C_5H_xCl_yF_z \qquad (5)$$

wherein "x" is an integer within a range from 0 to 10, each of "y" and "z" is an integer within a range from 1 to 11, x+y+z=12 or 10. This CFC or HCFC is chlorofluoropentane or chlorofluoropentene. Examples of this CFC are 1-chloroundecafluoropentane, 1,1,3-trichloro-1,2,2,3,4,4,5,5-nonafluoropentane, 1,1,1,2,2,4,4,5,5,5-decachloro-3,3-difluoropentane, 2,3-dichlorooctafluoropentene-1, and 3,4-dichloro-2-trifluoromethylpentafluorobutene-1.

Hydrogen atom(s) may be partly substituted for chlorine atom(s) of the above exemplary compounds of $C_5H_xCl_yF_z$.  These hydrogen-substituted compounds such as 1-chloro-1,1,2,2,3,3,4,4,5,5-decafluoropentane and a mixture(s) of the hydrogen-substituted compound(s) and the above exemplary compound(s) of $C_5H_xCl_yF_z$ may be used as a raw material equivalent to HCFC.

CFC or HCFC having six carbon atoms will be represented by the following general formula (6):

$$C_6H_xCl_yF_z \qquad (6)$$

wherein "x" is an integer within a range from 0 to 12, each of "y" and "z" is an integer within a range from 1 to 13, x+y+z=14 or 12. This CFC or HCFC is chlorofluorohexane or chlorofluorohexene. Examples of this CFC are 1-chlorotridecafluorohexane, 3,4-dichlorodecafluorohexane, 2,5-dichlorodecafluorohexane, 1,5-dichlorodecafluorohexane, 1,1,1-trichloroundecafluorohexane, 2,3,4,5,6,7-hexachlorooctafluorohexane, 1,1,1,3,4,6,6,6-octachlorohexafluorohexane, and isomers of these compounds.

Hydrogen atom(s) may be partly substituted for chlorine atom(s) of the above exemplary compounds of $C_6H_xCl_yF_z$. These hydrogen-substituted compounds and a mixture of the hydrogen-substituted compound(s) and the above exemplary compound(s) of $C_6H_xCl_yF_z$ may be used as a raw material equivalent to CFC. Examples of the hydrogen-substituted compounds of $C_6H_xCl_yF_z$ are 1-chloro-1,1,2,2,3,3,4,4,5,5,6,6-dodecafluorohexane and 1-chloro-2,2,3,3,4,4,4,5,5,6,6,6-undecafluorohexane.

The above-mentioned various examples of CFC or HCFC are preferably used in the preparation of HFC in which the number of fluorine atom is larger than the number of carbon atom.

The method of preparing CFC or HCFC is not particularly limited. One example of HCFC, 1,3-dichloro-1,1,2,2,3-pentafluoropropane (hereinafter, this compound will be referred to as HCFC225cb), is named as an alternative of the specified CFC. A method of preparing this HCFC225cb will be described in the following. Firstly, $CClF_2CF_2CCl_3$ which is an addition compound between tetrafluoroethylene and carbon tetrachloride is fluorinated by hydrogen fluoride so as to produce $CClF_2CF_2CCl_2F$. Then, this product is reduced by hydrogen to prepare HCFC225cb. Another method of preparing HCFC225cb will be described in the following. $CClF_2CF_2CCl_2F$ which is an addition compound between tetrafluoroethylene and trichlorofluoromethane is reduced by hydrogen to prepare HCFC225cb. Any of these chlorofluoropropanes as intermediate products may be used as a raw material of the method of the present invention.

Another example of CFC, 2,3-dichloro-1,1,1,4,4,4-hexafluorobutene-2, may be prepared by an arbitrary method. For example, this compound may be prepared by an coupling reaction of 1,1,1-trichloro-2,2,2-trifluoroethane (see JP-A-4-264040). As another example, this butene may be prepared by fluorinating 1,1,1,2,3,4,4,4-octachlorobutene-2 (see U.S. Pat. No. 2,554,857). In the invention, hydrogen may be partly or completely substituted for chlorine of this butene. The thus hydrogen-substituted butene has cis- and trans-form isomers. Either of these isomers or a mixture of these isomers may be used as a raw material of the method of the present invention. Similarly, either of cis and trans-form isomers or a mixture of these isomers of the above-exemplified compounds of CFC or HCFC may be used as a raw material of the method of the present invention.

A catalyst of the present invention which has palladium and bismuth may be used in the form of mixture of these metals itself. That is, the catalyst may take the form of powder, palladium black, metal wire netting or sol. However, it is general that the catalyst is carried on a carrier. Examples of the carrier are activated carbon, alumina, aluminum fluoride, partially fluorinated alumina, zirconia, partially fluorinated zirconia, calcium fluoride, silica, partially fluorinated silica, silica-alumina, titania and partially fluorinated titania. Of these, preferable examples are activated carbon, alumina, aluminum fluoride, partially fluorinated alumina and calcium fluoride. In particular, activated carbon is more preferable.

The amount of palladium is within a range from 0.01 to 20 wt % based on the weight of the carrier, and more preferably within a range from 0.1 to 10 wt %. If it is less than 0.01 wt %, the volume of a catalyst bed must be very large. This increases the production cost. If it is more than 20 wt %, it becomes difficult to make the catalyst uniformly dispersed on the carrier.

The catalyst of the present invention is superior in activity, selectivity and lifetime in the method of the present invention, by virtue of the combination of palladium and bismuth. This catalyst may further contain at least another element. In fact, this catalyst may contain at least one element selected from the group consisting of W, Re, Ta, Os, Mo, Ir, Ru, Nb and Hf, for the purpose of improving the catalyst lifetime. Furthermore, the catalyst may further contain at least one element selected from the group consisting of Tl, Sn, Cu, In, Cd, Ag, Pb, Hg, Hf, Zr, Mg, La and Ce, for the purpose of improving selectivity. Thus, a so-called ternary catalyst may be used in the present invention. Examples of this ternary catalyst are Pd/Bi/W (i.e. Pd, Bi and W), Pd/Bi/Re, Pd/Bi/Ta, Pd/Bi/Os, Pd/Bi/Mo, Pd/Bi/Ir, Pd/Bi/Ru, Pd/Bi/Nb, Pd/Bi/Hf, Pd/Bi/Tl, Pd/Bi/Sn, Pd/Bi/Cu, Pd/Bi/In, Pd/Bi/Cd, Pd/Bi/Ag, Pd/Bi/Pb, Pd/Bi/Hg, Pd/Bi/Zr, Pd/Bi/Mg, Pd/Bi/La, and Pd/Bi/Ce.

In the preparation of the mixture of Pd and Bi as the catalyst, it is preferable that the amount of Bi is within a range from 0.5 to 200 parts by weight relative to 100 parts by weight of Pd. The amount of Bi is more preferably within a range from 5 to 150 parts by weight, and still more preferably within a range from 20 to 100 parts by weight. By the addition of Bi to Pd, the yield increases; the catalyst deterioration is suppressed; and the temperature control of a reaction apparatus becomes easy. However, if the amount of Bi is less than 0.5 parts by weight, these advantages of the addition of Bi become hardly noticeable. If the amount of Bi is more than 200 parts by weight, the hydrogenation activity of the catalyst is lowered.

In case that another element is added to Pd and Bi, the amount of the another element relative to 100 parts by weight of Pd is preferably within a range from 0.5 to 200 parts by weight, more preferably within a range from 5 to 150 parts by weight, and still more preferably within a range from 20 to 100 parts by weight. If the amount of the another element is less than 0.5 parts by weight, an advantage of the addition of the another element such as suppression of the catalyst deterioration or the selectivity improvement becomes hardly noticeable. If the amount of the another element is more than 200 parts by weight, the hydrogenation activity of the catalyst is lowered.

A conventional method for carrying the metal on the carrier may be used in the present invention. As one example, at first, the carrier is immersed in a solution containing a palladium compound. Then, the wet carrier is air-dried, and then baked at a temperature within a range from 200° to 500° C. and preferably within a range from 250° to 400° C. so as to prepare a palladium-carried catalyst. Then, this catalyst is immersed in a solution containing a bismuth compound. Then, this wet carrier is air-dried, and then baked at a temperature within the same range as above so as to prepare a Pd- and Bi-carried catalyst. Furthermore, at least another optional element may be carried on the catalyst by the same process as above.

As another example of a method for carrying the metal on the carrier, at first, the carrier is immersed in a solution containing palladium and bismuth compounds and optionally at least another compound. Then, this wet carrier is air-dried, and then baked at a temperature within the same range as above so as to prepare the carried catalyst.

The palladium and bismuth compounds and the at least another compound are not limited to specific types as long as these compounds are soluble in a solvent(s). Examples of the palladium compound are palladium chloride, palladium nitrate, palladium sulfate, sodium tetrachloropalladate, palladium acetate, acetylacetonatopalladium, allylpalladium chloride, and tetrakis (triphenylphosphine)palladium. Examples of the bismuth compound are bismuth chloride, bismuth nitrate, and bismuth sulfate. Examples of the at least another compound are chlorides, nitrates, acetates, sulfates and oxides.

Examples of the solvent for the preparation of the catalyst are water, aqueous solutions such as ammonia, hydrochloric acid, nitric acid and sulfuric acid, organic solvents such as methanol, ethanol, acetone, methylene chloride, chloroform and benzene, and mixtures of these.

Prior to the hydrogenation of the present invention, it is necessary to reduce the metals carried on the carrier, in an atmosphere of hydrogen or in the presence of a reducing agent such as hydrazine, at a temperature within a range from 200° to 500° C. and preferably within a range from 300° to 500° C. If the temperature is lower than 200° C., the reduction does not occur sufficiently. If the temperature is higher than 500° C., sintering of the metals may proceed. This decreases the catalyst lifetime.

It is possible to conduct the hydrogenation of the present invention either in the gas phase or the liquid phase. If it is conducted in the gas phase, the reaction pressure is not particularly limited. However, it is usually within a range from 1 to 10 kg/cm$^2$. If it is less than 1 kg/cm$^2$, the size of the reaction vessel becomes too large. If it is more than 10 kg/cm$^2$, the mechanical strength of the reaction apparatus may become insufficient. The contact time of the hydrogenation in the gas phase is within a range from 0.5 to 200 seconds, preferably from 1 to 100 seconds, and more preferably from 2 to 60 seconds. It is necessary to adjust the contact time in accordance with the reaction temperature. However, if it is less than 0.5 seconds, conversion becomes insufficient. If it is more than 200 seconds, the degree of the hydrogenation proceeds too much.

The molar ratio of hydrogen gas to HCFC (gas) is within a range from y:1 to 20y:1, preferably from y:1 to 15y:1, more preferably from y:1 to 10y:1, and still more preferably from y:1 to 5y:1, wherein y is the number of chlorine atom in the above general formula (2). If the amount of hydrogen gas is too much, the recovery of hydrogen gas becomes cumbersome. Hydrogen gas serves to regenerate the catalyst, too. Thus, in case that HCFC is a saturated compound, the molar ratio of hydrogen gas to HCFC (gas) is preferably within a range from 1.0y:1 to 4.0y:1. In case that HCFC is an unsaturated compound, the molar ratio of hydrogen gas to HCFC (gas) is preferably within a range from 1.5y:1 to 5.0y:1. If desired, the reaction system may be diluted with an inert gas such as nitrogen, argon or helium.

The reaction temperature of the hydrogenation relates to conversion of HCFC, the catalyst lifetime and the boiling point of HCFC. In case that HCFC has a boiling point not higher than 70° C., the reaction temperature is within a range from 70° to 400° C., preferably from 90° to 350° C., more preferably from 100° to 300° C., and still more preferably from 100° to 250° C. If the reaction temperature is lower than 70° C. or the boiling point of HCFC, a special apparatus for conducting the hydrogenation under reduced pressure is necessary for vaporizing HCFC. If the reaction temperature is higher than 400° C., sintering of the catalyst proceeds, thereby decreasing the catalyst lifetime.

Another case in which the hydrogenation is conducted in a liquid phase will be described in the following. In this case, the hydrogenation is conducted in the presence of a solvent inactive in the hydrogenation, such as water, diethyl ether, tetrahydrofuran, methanol, ethanol or isopropanol, or without using such solvent. The reaction pressure is not particularly limited, but is generally within a range from 1 to 100 kg/cm$^2$. If it is less than 1 kg/cm$^2$, the size of the reaction vessel becomes too large. If it is more than 100 kg/cm$^2$, the apparatus may become insufficient in mechanical strength. The reaction temperature relates to conversion of HCFC and the catalyst lifetime. The reaction temperature is within a range from 20° to 200° C., and preferably from 30° to 150° C. If it is lower than 20° C., the reaction takes too much time. If it is higher than 200° C., the degree of hydrogenation proceeds too much. The reaction time is not particularly limited, but is generally within a range from 30 minutes to 10 hr. The reaction may be conducted by either a batch process or a flow process.

The following examples are illustrative of the present invention, but these examples are not limitative.

PREPARATION OF CATALYST

The following Examples 1–10 are illustrative of the preparation of catalyst in accordance with the present invention, and the following Comparative Examples 1–2 are illustrative of the preparation of catalyst not in accordance with the present invention.

EXAMPLE 1

In this example, a catalyst having Bi and Pd was prepared as follows. At first, 0.10 g of Bi(NO$_3$)$_3$.5H$_2$O was dissolved in 200 cc of pure water so as to prepare a solution. Then, 200 cc of a commercial 0.5% palladium-carrying activated carbon made by N.E. Chem Cat Co. was immersed in the solution for 20 hr. Then, the carried catalyst was dried by an evaporator. Then, the catalyst was air-dried, and then baked at a temperature of 300° C. for 2.5 hr. Thus prepared catalyst had 10 wt % of Bi based on the total weight of palladium.

EXAMPLE 2

In this example, Example 1 was repeated except in that only 0.05 g of Bi(NO$_3$)$_3$.5H$_2$O was used. The thus prepared catalyst had 5 wt % of Bi based on the total weight of palladium.

EXAMPLE 3

In this example, a catalyst having Pd and Bi was prepared as follows. At first, 20.2 g of Bi(NO$_3$)$_3$.5H$_2$O and 100 cc of 35% HCl were added to 100 cc of pure water maintained at a temperature of 70° C. This mixture was sufficiently stirred so as to prepare a first solution. Separately, 33.8 g of palladium chloride and 100 cc of 35% HCl were added to 100 cc of pure water maintained at 70° C. This mixture was sufficiently stirred so as to prepare a second solution. Separately, 1100 cc of pure water was added to a round bottom flask. Then, 405 g of a commercial activated carbon (3I (trade name) made by Nikki Chemical Co.) was immersed into the water of the flask. Then, the flask was allowed to stand still for one day. The first and second solutions were mixed together, and then this mixture was sufficiently stirred. Then, this mixture was added to the flask. Then, the flask was again allowed to stand still for one day. Then, water in the flask was evaporated by an evaporator so as to get a dried solid matter. Then, this solid matter was further dried at a temperature of 120° C. for 2 hr with a hot-air drier, and then baked at 300° C. for 3 hr so as to prepare a catalyst having Pd and Bi carried on activated carbon. The amount of Pd was 5 wt % based on the total weight of activated carbon. The amount of Bi was 43 wt % based on the total weight of Pd.

EXAMPLE 4

In this example, Example 3 was modified as follows with respect to the amounts of raw materials. At first, 2.02 g of Bi(NO$_3$)$_3$.5H$_2$O and 10 cc of 35% HCl were added to 10 cc of pure water maintained at a temperature of 70° C. This mixture was sufficiently stirred so as to prepare a first solution. Separately, 3.38 g of palladium chloride and 10 cc of 35% HCl were added to 100 cc of pure water maintained at 70° C. This mixture was sufficiently stirred so as to prepare a second solution. Separately, 110 cc of pure water was added to a round bottom flask. Then, 40.5 g of a commercial activated carbon (3I made by Nikki Chemical Co.) was immersed into the water of the flask. Then, the flask was allowed to stand still for one day. The first and second solutions were mixed together, and then this mixture was sufficiently stirred. Then, this mixture was added to the flask. Then, the flask was again allowed to stand still for one day. Then, water in the flask was evaporated by an evaporator to get a dried solid matter. Then, this dried solid matter was further dried at a temperature of 120° C. for 2 hr with a hot-air drier, and then baked at 300° C. for 3 hr so as to prepare a catalyst having Pd and Bi carried on activated carbon. The amount of Pd was 5 wt % based on the total weight of activated carbon. The amount of Bi was 43 wt % based on the total weight of Pd.

EXAMPLE 5

In this example, a catalyst having Pd, Bi and Hf carried on activated carbon was prepared as follows. At first, 0.20 g of $Bi(NO_3)_3 \cdot 5H_2O$ and 10 cc of 35% HCl were added to 10 cc of pure water maintained at a temperature of 70° C. This mixture was sufficiently stirred so as to prepare a first solution. Separately, 0.34 g of palladium chloride and 1 cc of 35% HCl were added to 10 cc of pure water maintained at 70° C. This mixture was sufficiently stirred so as to prepare a second solution. Separately, 0.15 g of hafnium chloride and 1 cc of 35% HCl were added to 10 cc of pure water maintained at a temperature of 70° C. This mixture was sufficiently stirred so as to prepare a third solution. Separately, 110 cc of pure water was added to a round bottom flask. Then, 40.5 g of a commercial activated carbon (3I made by Nikki Chemical Co.) was immersed into the water of the flask. Then, the flask was allowed to stand still for one day. The first, second and third solutions were mixed together, and then this mixture was sufficiently stirred. Then, this mixture was added to the flask. Then, the flask was again allowed to stand still for one day. Then, water in the flask was evaporated by an evaporator to get a dried solid matter. Then, this solid matter was further dried at a temperature of 120° C. for 2 hr with a hot-air drier, and then baked at 300° C. for 3 hr so as to prepare a catalyst having Pd, Bi and Hf carried on activated carbon. The amount of Pd was 0.5 wt % based on the total weight of activated carbon. The amount of each of Bi and Hf was 43 wt % based on the total weight of Pd.

EXAMPLES 6-9

In these examples, Example 5 was repeated except in that other elements were used in place of hafnium chloride. In fact, in Examples 6-9, niobium chloride, magnesium chloride, zirconium chloride and molybdenum oxide were respectively used as alternative compounds in place of hafnium chloride. In each of Examples 6-9, the amount of Pd was 0.5 wt % based on the total weight of activated carbon, the amounts of Bi and each of these alternative compounds were respectively 43 wt % based on the total weight of Pd.

EXAMPLE 10

In this example, Example 5 was repeated except in that the third solution containing hafnium chloride was omitted.

Therefore, a catalyst having Pd and Bi carried on activated carbon was prepared.

Comparative Example 1

In this example, a catalyst having only Pd carried on activated carbon was prepared as follows. At first, 0.34 g of palladium chloride and 10 cc of 35% HCl were added to 10 cc of pure water maintained at 70° C. This mixture was sufficiently stirred so as to prepare a palladium chloride solution. Separately, 110 cc of pure water was added to a round bottom flask. Then, 40.5 g of a commercial activated carbon (3I made by Nikki Chemical Co.) was immersed into the water of the flask. Then, the flask was allowed to stand still for one day. Then, the palladium chloride solution was added to the flask. This mixture in the flask was sufficiently stirred, and then the flask was again allowed to stand still for one day. Then, water in the flask was evaporated by an evaporator to get a dried solid matter. Then, this solid matter was further dried at a temperature of 120° C. for 2 hr with a hot-air drier, and then baked at 300° C. for 3 hr so as to prepare a catalyst having only Pd carried on activated carbon. The amount of Pd was 0.5 wt % based on the total weight of activated carbon.

Comparative Example 2

In this comparative example, Example 5 was repeated except in that zirconium chloride was used in place of hafnium chloride and that the first solution containing bismuth nitrate was omitted. In fact, a catalyst having Pd and Zr carried on activated carbon was prepared in this comparative example. The amount of palladium was 0.5 wt % based on the total weight of activated carbon. The amount of zirconium was 43 wt % based on the total weight of palladium.

PREPARATION OF HFC

The following Examples 11-51 are illustrative of the preparation of HFC in accordance with the present invention, and the following Comparative Examples 3-7 are illustrative of the preparation of HFC not in accordance with the present invention.

EXAMPLE 11

At first, a reactor (a 2.5 cm ID, 40 cm long quartz tube) equipped with an electric furnace was charged with 50 cc of the catalyst (Bi+Pd) prepared in accordance with Example 1. Then, the reactor was gradually heated to a temperature of 400° C., while hydrogen gas at a flow rate of 80 cc/min was passed through for 2 hrs. to reduce the catalyst. Then, the temperature was lowered to 320° C., and a mixture of HCFC225cb and hydrogen (1:4 in the molar ratio) was passed through the reactor. The contact time was 30 seconds. 2 hrs after the start of the reaction, the product leaving the reactor were analyzed by gas chromatography. The analytical results shown in Table 1 illustrate the high conversion of HCFC225cb and the high selectivity of HFC245ca (1,1,2,2,3-pentafluoropuropane).

EXAMPLE 12

In this example, Example 11 was repeated except in that the reaction temperature was 300° C. instead of 320° C. The result of gas chromatography is shown in Table 1.

EXAMPLE 13

In this example, Example 11 was repeated except in that the flow rate of hydrogen gas was 60 cc/min in place of 80 cc/min and that the contact time was 38 seconds in place of 30 seconds. The result of gas chromatography is shown in Table 1.

EXAMPLE 14

In this example, Example 11 was repeated except in that the catalyst prepared in accordance with Example 2 was used in place of that of Example 1. The result of gas chromatography is shown in Table 1.

Comparative Example 3

In this example, Example 11 was repeated except in that a commercial 0.5% palladium-carrying activated carbon was used as a catalyst. As is the same as Example 11, 2 hrs after the start of the reaction, the products leaving the reactor were analyzed by gas chromatography. The result of this analysis is shown in Table 1. 10 hr after the start of the reaction, the same analysis was conducted. With this, the selectivity of HFC245ca was 60% which is almost the same as that shown in Table 1, but the conversion of HCFC225cb decreased to 30% and the catalyst deterioration was confirmed.

TABLE 1

| Reaction Products (wt %) | Ex. 11 | Ex. 12 | Ex. 13 | Ex. 14 | Com. Ex. 3 |
| --- | --- | --- | --- | --- | --- |
| HFC245ca | 87.0 | 68.7 | 84.4 | 82.5 | 60.3 |
| HCFC235cc* | 4.9 | 23.6 | 8.0 | 5.1 | 25.8 |
| HCFC235ca** | 0.1 | 1.8 | 0.5 | 0.1 | 1.1 |
| HCFC225cb | traces | traces | traces | traces | traces |
| Others | 8.0 | 5.9 | 7.1 | 12.3 | 12.8 |
| Conversion (%) | 100 | 100 | 100 | 100 | 100 |
| Selectivity (%) | 87.0 | 68.7 | 84.4 | 82.5 | 60.3 |

*HCFC235cc: 1-chloro-1,1,2,2,3-pentafluoropropane
**HCFC235ca: 3-chloro-1,1,2,2,3-pentafluoropropane

EXAMPLE 15

In this example, Example 11 was modified as follows. At first, a reactor (a 3.7 cm ID, 110 cm long quartz tube) equipped with an electric furnace was charged with 900 cc of the catalyst (Bi+Pd) prepared in accordance with Example 3. Then, the reactor was gradually heated to a temperature of 400° C., while hydrogen gas at a flow rate of 2,000 cc/min was passed through for 2 hrs to reduce the catalyst. Then, the temperature was lowered to 240° C., and a mixture of HCFC225cb at a flow rate of 0.96 mol/hr and hydrogen at a flow rate of 3.86 mol/hr was passed through the reactor via a vaporizer and a mixer. The contact time was 30 seconds. After confirming a constant condition of the products leaving the reactor, the products were analyzed by gas chromatography. The analytical results shown in Table 2 illustrate the high conversion of HCFC225cb and the high selectivity of HFC245ca.

EXAMPLES 16-21

In each of these examples, Example 15 was repeated except in that the reaction conditions were modified as shown in Table 2. In each of Examples 16-21, after confirming a constant condition of the products leaving the reactor, the products were analyzed with gas chromatography. The analytical results shown in Table 2 illustrate the high conversion of HCFC225cb and the high selectivity of HFC245ca.

EXAMPLE 22

In this example, Example 15 was modified as follows. At first, the same catalyst as that of Example 15 was reduced under the same condition as that of Example 15. Then, the temperature was lowered to 240° C., and a mixture of HCFC225cb at a flow rate of 1.49 mol/hr and hydrogen at a flow rate of 6.02 mol/hr was passed through the reactor via a vaporizer and a mixer. Then, the reaction temperature was maintained at 280° C. by adjusting the temperature of the electric furnace. The contact time was 19 seconds. 102 hr after the start of the reaction, the products leaving the reactor were analyzed by gas chromatography. The analytical results are shown in Table 2. These results were almost the same as those immediately after the start of the reaction, with respect to the reaction products composition, the conversion of HCFC225cb and the selectivity of HFC245ca.

TABLE 2

|  | Ex. 15 | Ex. 16 | Ex. 17 | Ex. 18 | Ex. 19 | Ex. 20 | Ex. 21 | Ex. 22 |
| --- | --- | --- | --- | --- | --- | --- | --- | --- |
| Reaction Conditions |  |  |  |  |  |  |  |  |
| Reaction Temp. (°C.) | 240 | 250 | 260 | 270 | 280 | 280 | 280 | 280 |
| Flow Rate of HCFC225cb (mol/hr) | 0.96 | 0.96 | 0.96 | 0.96 | 0.96 | 0.48 | 1.44 | 1.49 |
| Flow Rate of Hydrogen (mol/hr) | 3.86 | 3.86 | 3.86 | 3.86 | 3.86 | 1.93 | 5.79 | 6.02 |
| Contact Time (s) | 30 | 30 | 30 | 30 | 30 | 60 | 20 | 19 |
| Reaction Products (wt %) |  |  |  |  |  |  |  |  |
| HFC245ca | 76.3 | 84.8 | 90.7 | 92.3 | 93.5 | 94.2 | 90.2 | 93.7 |
| HCFC235cc* | 16.4 | 8.7 | 1.7 | 1.6 | 0.1 | traces | 2.9 | 0.4 |
| HCFC235ca** | 1.0 | 0.5 | traces | traces | traces | traces | traces | traces |
| HCFC225cb | 0.1 | traces | 0.6 | 0.5 | traces | traces | traces | traces |
| Others | 6.2 | 6.0 | 7.0 | 5.6 | 6.4 | 5.8 | 6.9 | 5.9 |
| Conversion (%) | 99.9 | 100 | 99.4 | 99.5 | 100 | 100 | 100 | 100 |
| Selectivity (%) | 76.4 | 84.8 | 91.2 | 92.8 | 93.5 | 94.2 | 90.2 | 93.7 |

*HCFC235cc: 1-chloro-1,1,2,2,3-pentafluoropropane
**HCFC235ca: 3-chloro-1,1,2,2,3-pentafluoropropane

EXAMPLE 23

In this example, Example 11 was repeated except in that the reaction temperature was 250° C. and that 3,3-dichloro-1,1,1,2,2-pentafluoropropane (hereinafter, this compound will be referred to as HCFC225ca) was used as HCFC. The analytical results shown in Table 3 illustrate the high conversion of HCFC225ca and the high selectivity of HFC245cb (1,1,1,2,2-pentafluoro-propane).

EXAMPLE 24

In this example, Example 23 was repeated except in that the reaction temperature was 230° C. The analytical result is shown in Table 3.

Comparative Example 4

In this example, Example 23 was repeated except in that a commercial 0.5% palladium-carrying active carbon was used as a catalyst. The analytical result is shown in Table 3.

TABLE 3

|  | Ex.23 | Ex.24 | Com.Ex.4 |
|---|---|---|---|
| Reaction Products (wt %) |  |  |  |
| HFC245cb* | 71.0 | 57.0 | 48.6 |
| HCFC235cb** | 15.4 | 31.4 | 25.8 |
| HCFC254ea*** | 9.8 | 9.1 | 15.1 |
| HCFC225ca | traces | traces | traces |
| Others | 3.8 | 2.5 | 10.5 |
| Conversion (%) | 100 | 100 | 100 |
| Selectivity (%) | 71.0 | 57.0 | 48.6 |

*HFC245cb: 1,1,1,2,2-pentafluoropropane
**HCFC235cb: 3-chloro-1,1,1,2,2-pentafluoropropane
***HCFC254ea: 1,1,1,2-tetrafluoropropane

EXAMPLE 25

In this example, Example 23 was modified as follows. At first, a reactor (a 1.4 cm ID, 50 cm long stainless steel tube) equipped with an electric furnace was charged with 40 cc of the catalyst (Bi+Pd) prepared in accordance with Example 4. Then, the reactor was gradually heated to a temperature of 400° C., while hydrogen gas at a flow rate of 100 cc/min was passed through for 2 hrs to reduce the catalyst. Then, the temperature was lowered to 260° C., and a mixture of 1,3-dichloro-1,1,2,2,3,3-hexafluoropropane (hereinafter, this compound will be referred to as HCFC216ca) at a flow rate of 20 cc/min and hydrogen at a flow rate of 60 cc/min was passed through the reactor via a vaporizer and a mixer. Then, the reaction temperature was maintained at 280° C. by adjusting the temperature of the electric furnace. The contact time was 30 seconds. After confirming a constant condition of the products leaving the reactor, the products were analyzed by gas chromatography. The analytical results shown in Table 4 illustrate the high conversion of HCFC216ca and the high selectivity of HFC236ca.

Comparative Example 5

In this comparative example, Example 25 was repeated except in that a catalyst (only Pd) of Comparative Example 1 was used. The analytical results are shown in Table 4.

EXAMPLES 26–28

In each of these examples, Example 25 was repeated except in that the reaction conditions were modified as shown in Table 4.

TABLE 4

|  | Com. Ex. 5 | Ex. 25 | Ex. 26 | Ex. 27 | Ex. 28 |
|---|---|---|---|---|---|
| Reaction Conditions |  |  |  |  |  |
| Reaction Temp. (°C.) | 260 | 260 | 280 | 300 | 280 |
| Flow Rate of HCFC216ca* (cc/min) | 10 | 10 | 10 | 10 | 20 |
| Flow Rate of Hydrogen (cc/min) | 60 | 60 | 60 | 60 | 120 |
| Contact Time (s) | 30 | 30 | 30 | 30 | 15 |
| Reaction Products (wt %) |  |  |  |  |  |
| HFC245ca** | 22.9 | 0.5 | 1.1 | 2.3 | 0.8 |
| HFC236ca*** | 65.7 | 88.0 | 93.1 | 93.6 | 76.3 |
| HCFC226ca**** | 5.3 | 5.1 | 2.0 | 0.1 | 2.2 |
| HCFC216ca and Others | 6.1 | 6.4 | 3.8 | 4.0 | 19.7 |
| Conversion (%) | 92.8 | 95.1 | 99.6 | 99.8 | 85.7 |
| Selectivity (%) | 70.8 | 92.5 | 93.5 | 93.8 | 89.0 |

*HCFC216ca: 1,3-dichloro-1,1,2,2,3,3-hexafluoropropane
**HFC245ca: 1,1,2,2,3-pentafluoropropane
***HFC236ca: 1,1,2,2,3,3-hexafluoropropane
****HCFC226ca: 1-chloro-1,1,2,2,3,3-hexafluoropropane

EXAMPLE 29

In this example, Example 25 was repeated except in that the temperature of the reactor was decreased from 400° C. (the catalyst reduction temperature) to 280° C. (the reaction temperature), that 1,1,3-trichloro-1,2,2,3,3-pentalfuoropropane (hereinafter, this compound will be referred to as HCFC215ca) was used as HCFC. The analytical results are shown in Table 5.

Comparative Example 6

In this comparative example, Example 29 was repeated except in that a catalyst (only Pd) of Comparative Example 1 was used. The analytical results are shown in Table 5.

EXAMPLES 30–32

In each of these examples, Example 29 was repeated except in that the reaction conditions were modified as shown in Table 5.

TABLE 5

|  | Com. Ex. 6 | Ex. 29 | Ex. 30 | Ex. 31 | Ex. 32 |
|---|---|---|---|---|---|
| Reaction Conditions |  |  |  |  |  |
| Reaction Temp. (°C.) | 280 | 280 | 300 | 300 | 300 |
| Flow Rate of HCFC215ca* (cc/min) | 10 | 10 | 10 | 5 | 20 |
| Flow Rate of Hydrogen (cc/min) | 60 | 60 | 60 | 30 | 120 |
| Contact Time (s) | 30 | 30 | 30 | 60 | 15 |
| Reaction Products (wt %) |  |  |  |  |  |
| HFC254ca** | 18.8 | 3.0 | 3.3 | 1.2 | 3.8 |
| HFC245ca*** | 64.0 | 88.9 | 91.1 | 94.7 | 78.8 |
| HCFC235ca**** | 5.3 | 1.4 | 0.8 | 0.1 | 2.0 |
| HCFC215ca and Others | 11.9 | 6.7 | 4.8 | 4.0 | 5.4 |
| Conversion (%) | 93.8 | 94.7 | 98.4 | 99.6 | 95.1 |
| Selectivity (%) | 68.2 | 93.9 | 92.6 | 95.1 | 82.9 |

*HCFC215ca: 1,1,3-trichloro-1,2,2,3,3-pentafluoropropane
**HFC254ca: 1,2,2,3-tetrafluoropropane
***HFC245ca: 1,1,2,2,3-pentafluoropropane
****HCFC235ca: 1-chloro-1,2,2,3,3-pentafluoropropane

EXAMPLE 33

In this example, Example 25 was substantially repeated except in that the temperature of the reactor was decreased from 400° C. (the catalyst reduction temperature) to 200° C. (the reaction temperature), that 2,3-dichloro-1,1,1,4,4,4-hexafluorobutene-2 (hereinafter, this compound will be referred to as 1316) was used as CFC, and that the flow rates of 1316 and hydrogen gas were respectively 10 cc/min and 70 cc/min. 2 hr after the start of the reaction, the composition of the reaction products became stable and the products leaving the reactor were analyzed by gas chromatography. The analytical results are shown in Table 6.

EXAMPLES 34–42

In each of these examples, Example 33 was repeated except in that the reaction conditions were modified as shown in Table 6. After a constant condition of the products leaving the reactor was confirmed, the products were analyzed by gas chromatography. The analytical results are shown in Table 6.

EXAMPLE 43

In this example, Example 39 was repeated except in that the reaction time was prolonged by 50 hrs. In other words, the reaction time was about 100 hrs in total. After the completion of this reaction time, the products leaving the reactor were analyzed by gas chromatography. The analytical results shown in Table 6 illustrate no deterioration of the catalyst.

EXAMPLE 44–45

In each of these examples, Example 34 was repeated except in that the reaction conditions were modified as shown in Table 6.

TABLE 6

| | Reaction Temp (°C.) | Flow Rate of HCFC (cc/min) | Flow Rate of $H_2$ (cc/min) | Contact Time (s) | Reaction Product Composition (%) | | |
|---|---|---|---|---|---|---|---|
| | | | | | 356* | 1326** | 1316*** |
| Ex. 33 | 200 | 10 | 70 | 30 | 97.9 | 0.16 | traces**** |
| Ex. 34 | 200 | 20 | 140 | 15 | 97.7 | 0.12 | 0.04 |
| Ex. 35 | 200 | 30 | 210 | 10 | 97.7 | 0.16 | 0.04 |
| Ex. 36 | 200 | 40 | 280 | 7.5 | 97.6 | 0.14 | 0.08 |
| Ex. 37 | 120 | 40 | 280 | 7.5 | 96.2 | 0.07 | 1.21 |
| Ex. 38 | 130 | 40 | 280 | 7.5 | 96.8 | 0.08 | 0.29 |
| Ex. 39 | 150 | 40 | 280 | 7.5 | 97.5 | 0.09 | 0.03 |
| Ex. 40 | 150 | 70 | 250 | 7.5 | 97.3 | 0.18 | 0.03 |
| Ex. 41 | 150 | 80 | 240 | 7.5 | 97.2 | 0.16 | 0.05 |
| Ex. 42 | 170 | 80 | 240 | 7.5 | 97.7 | 0.19 | 0.05 |

TABLE 6-continued

| | Reaction Temp (°C.) | Flow Rate of HCFC (cc/min) | Flow Rate of $H_2$ (cc/min) | Contact Time (s) | Reaction Product Composition (%) | | |
|---|---|---|---|---|---|---|---|
| | | | | | 356* | 1326** | 1316*** |
| Ex. 43 | 150 | 40 | 280 | 7.5 | 97.6 | 0.08 | 0.04 |
| Ex. 44 | 140 | 40 | 280 | 7.5 | 96.3 | 0.05 | traces**** |
| Ex. 45 | 180 | 40 | 280 | 7.5 | 93.5 | 0.07 | traces**** |

*356: 1,1,1,4,4,4-hexafluorobutane
**1326: 2-chloro-1,1,1,4,4,4-hexafluorobutene-2
***1316: 2,3-dichloro-1,1,1,4,4,4-hexafluorobutene-2
****traces: an amount not higher than 200 ppm

EXAMPLE 46

In this example, Example 23 was modified as follows. At first, a reactor (a 2.8 cm ID, 16 cm long stainless steel tube) equipped with an electric furnace was charged with 100 cc of the catalyst (Bi+Pd) prepared in accordance with Example 10. Then, the reactor was gradually heated to a temperature of 400° C., while hydrogen gas at a flow rate of 100 cc/min was passed through for 2 hrs to reduce the catalyst. Then, the temperature was lowered to 300° C., and a mixture of HCFC at a flow rate of 40 cc/min and hydrogen at a flow rate of 160 cc/min was passed through the reactor via a vaporizer and a mixer. Then, the reaction temperature was maintained at 330° C. by adjusting the temperature of the electric furnace. The contact time was 30 seconds. After confirming a constant condition of the products leaving the reactor, the products were analyzed by gas chromatography. The analytical results are shown in Table 7.

EXAMPLES 47–51

In each of these examples, Example 46 was repeated except in that the catalyst type was modified as shown in Table 7 and that the reaction conditions were modified as shown in Table 7. In fact, the catalysts prepared in accordance with Examples 8, 7, 9, 6 and 5 were respectively used in Examples 47–51.

Comparative Example 7

In this example, Example 46 was repeated except in that the reaction conditions were modified as shown in Table 7 and that the catalyst (Pd+Zr) of Comparative Example 2 was used.

TABLE 7

| | Ex. 46 | Ex. 47 | Ex. 48 | Ex. 49 | Ex. 50 | Ex. 51 | Com. Ex. 7 |
|---|---|---|---|---|---|---|---|
| Reaction Conditions | | | | | | | |
| Catalyst Type | Pd/Bi | Pd/Bi/Zr | Pd/Bi/Mg | Pd/Bi/Mo | Pd/Bi/Nb | Pd/Bi/Hf | Pd/Zr |
| Reaction Temp. (°C.) | 320 | 340 | 320 | 340 | 310 | 330 | 340 |
| Flow Rate of HCFC225cb (cc/min) | 40 | 40 | 40 | 40 | 40 | 40 | 40 |
| Flow Rate of Hydrogen (cc/min) | 160 | 160 | 160 | 160 | 160 | 160 | 160 |
| Contact Time (s) | 30 | 30 | 30 | 30 | 30 | 30 | 30 |
| Reaction Products (wt %) | | | | | | | |
| HFC245ca* | 84.5 | 79.3 | 78.4 | 51.7 | 59.5 | 78.1 | 4.0 |
| HCFC235** | 0.8 | 7.0 | 12.9 | 32.4 | 23.3 | 1.1 | 46.5 |
| HCFC225cb and Others | traces | 0.2 | traces | 0.2 | 0.3 | 0.1 | 44.7 |

TABLE 7-continued

|  | Ex. 46 | Ex. 47 | Ex. 48 | Ex. 49 | Ex. 50 | Ex. 51 | Com. Ex. 7 |
|---|---|---|---|---|---|---|---|
| Conversion (%) | 100 | 99.8 | 100 | 99.8 | 99.7 | 99.9 | 55.3 |
| Selectivity (%) | 84.5 | 79.5 | 78.4 | 51.8 | 59.7 | 78.2 | 7.2 |

*HCFC235ca: 1,1,2,2,3-pentafluoropropane
**HCFC235: the total of HCFC235cc and HCFC235ca

What is claimed is:

1. A method of preparing a saturated hydrofluorocarbon represented by the following general formula (1), the method comprising the step of:

reducing a chlorofluorocarbon or hydrochlorofluorocarbon represented by the following general formula (2), by hydrogen in a gas phase in the presence of a catalyst comprising elemental palladium and elemental bismuth, said catalyst being carried on a carrier,

$$C_nH_pF_z \quad (1)$$

$$C_nH_xCl_yF_z \quad (2)$$

wherein "n" is an integer within a range from 3 to 6, "x" is an integer within a range from 0 to 2n, each of "y" and "z" is an integer within a range from 1 to 2n+1, x+y+z=2n+2 or 2n, p=x+y when x+y+z=2n+2, and p=x+y+2 when x+y+z=2n, wherein, before said step, said palladium and said bismuth are reduced at a temperature within a range from 200° to 500° C., in an atmosphere of hydrogen gas or in the presence of a reducing agent, and wherein said chlorofluorocarbon or hydrochlorofluorocarbon and said hydrogen are respectively in the form of gas, and wherein said catalyst is in the form of solid.

2. A method according to claim 1, wherein said chlorofluorocarbon or hydrochlorofluorocarbon is one compound selected from the group consisting of 1,3-dichloro-1,1,2,2,3-pentafluoropropane, 3,3-dichloro-1,1,1,2,2-pentafluoropropane, 1,3-dichloro-1,1,2,2,3,3-hexafluoropropane, 1,1,3-trichloro-1,2,2,3,3-pentafluoropropane and 2,3-dichloro-1,1,1,4,4,4-hexafluorobutene-2.

3. A method according to claim 1, wherein said carrier is activated carbon.

4. A method according to claim 1, wherein the amount of said palladium carried on said carrier is within a range from 0.01 to 20 wt % based on the total weight of said carrier.

5. A method according to claim 1, wherein the weight ratio of said bismuth to said palladium is within a range from 0.5:100 to 200:100.

6. A method according to claim 1, wherein the number of fluorine atoms of said hydrofluorocarbon is larger than the number of carbon atoms of said hydrofluorocarbon.

7. A method according to claim 6, wherein said hydrofluorocarbon is one member selected from the group consisting of 1,1,2,2,3-pentafluoropropane, 1,1,1,2,2-pentafluoropropane, 1,1,2,2,3,3-hexafluoropropane, 1,1,2,2,3-pentafluoropropane, and 1,1,1,4,4,4-hexafluorobutane.

8. A method according to claim 6, wherein said hydrofluorocarbon and said hydrochlorofluorocarbon are 1,1,2,2,3-pentafluoropropane and 1,3-dichloro-1,1,2,2,3-pentafluoropropane, respectively.

9. A method according to claim 6, wherein said hydrofluorocarbon and said hydrochlorofluorocarbon are 1,1,1,2,2-pentafluoropropane and 3,3-dichloro-1,1,1,2,2-pentafluoropropane, respectively.

10. A method according to claim 6, wherein said hydrofluorocarbon and said chlorofluorocarbon are 1,1,2,2,3,3-hexafluoropropane and 1,3-dichloro-1,1,2,2,3,3-hexafluoropropane, respectively.

11. A method according to claim 6, wherein said hydrofluorocarbon and said chlorofluorocarbon are 1,1,2,2,3-pentafluoropropane and 1,1,3-trichloro-1,2,2,3,3-pentafluoropropane, respectively.

12. A method according to claim 6, wherein said hydrofluorocarbon and said chlorofluorocarbon are 1,1,1,4,4,4-hexafluorobutane and 2,3-dichloro-1,1,1,4,4,4-hexafluorobutene-2, respectively.

13. A method according to claim 1, wherein said catalyst further comprises at least one element selected from the group consisting of W, Re, Ta, Os, Mo, Ir, Ru, Nb, Hf, Tl, Sn, Cu, In, Cd, Ag, Pb, Hg, Hf, Zr, Mg, La, and Ce.

14. A method according to claim 13, wherein the weight ratio of said at least one element to said palladium is within a range from 0.5:100 to 200:100.

15. A method according to claim 1, wherein, when said chlorofluorocarbon or hydrochlorofluorocarbon in the form of gas is reduced in said step and said chlorofluorocarbon or hydrochlorofluorocarbon has a boiling point not higher than 70° C., said step is conducted at a temperature within a range from 70° to 400° C.

* * * * *